United States Patent [19]

Ogino et al.

[11] Patent Number: 4,678,598
[45] Date of Patent: Jul. 7, 1987

[54] LIQUID SHAMPOO COMPOSITION

[75] Inventors: Hidekazu Ogino, Funabashi; Hajime Hirota, Tokyo, both of Japan

[73] Assignee: Kao Corporation, Tokyo, Japan

[21] Appl. No.: 890,547

[22] Filed: Jul. 30, 1986

[30] Foreign Application Priority Data

Aug. 6, 1985 [JP] Japan ................................ 60-172992
Sep. 17, 1985 [JP] Japan ................................ 60-204981

[51] Int. Cl.⁴ ........................ C11D 3/22; C11D 17/08
[52] U.S. Cl. .............................. 252/174.17; 252/89.1; 252/106; 252/DIG. 2; 252/DIG. 5; 252/DIG. 13; 252/DIG. 14; 424/70; 536/103
[58] Field of Search ......... 252/89.1, DIG. 13, 174.17, 252/DIG. 14, 106, 173, DIG. 2, DIG. 5; 536/103; 424/70

[56] References Cited

U.S. PATENT DOCUMENTS

| | | | |
|---|---|---|---|
| 3,565,887 | 2/1971 | Parmerter | 252/108 |
| 4,265,779 | 5/1981 | Gandolfo et al. | 252/174.21 |
| 4,352,794 | 10/1982 | Kock | 536/103 |
| 4,472,297 | 9/1984 | Bolich, Jr. et al. | 252/DIG. 13 |
| 4,507,319 | 3/1985 | Barratt et al. | 514/546 |
| 4,564,462 | 1/1986 | Watanabe et al. | 252/108 |

*Primary Examiner*—Paul Lieberman
*Assistant Examiner*—Hoa Van Le
*Attorney, Agent, or Firm*—Oblon, Fisher, Spivak, McClelland & Maier

[57] ABSTRACT

Novel liquid shampoo compositions comprise the following components (A), (B) and (C):

(A) 5 to 30 wt % of at least one surface active agent,
(B) 0.05 to 5 wt % of a skin sensation inducing aromatic chemical such as menthol and camphor, and
(C) $\frac{1}{2}$ to twenty times by weight based on the amount of component (B) of a modified cyclodextrin, represented by the following formula (I) or (II):

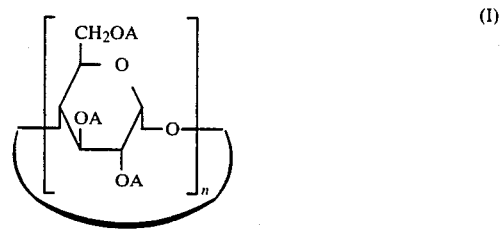

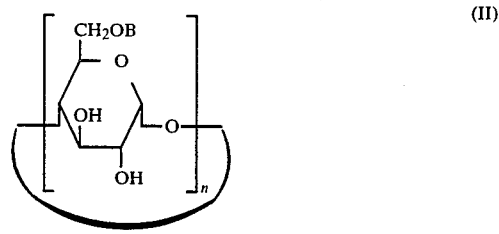

The shampoo compositions in which the specific odor of component (B) is effectively depressed by component (C) have a sufficient pharmaceutical effect on use and have good stability at low temperature.

6 Claims, No Drawings

LIQUID SHAMPOO COMPOSITION

BACKGROUND OF THE INVENTION

1. Field of the Invention

This invention relates to a liquid shampoo composition, and particularly to such composition in which the specific odor of a skin sensation inducing aromatic chemical contained in the composition is effectively depressed while a sufficient pharmaceutical effect on use being assured, and which has good stability at low temperatures.

2. Description of the Prior Art

In the hair care industry, it has been a conventional practice that about 1% of a skin sensation inducing aromatic chemical, such as menthol, is incorporated into a shampoo composition expecting its pharmaceutical effect obtainable during or after the hair wash.

These shampoos, generally called "tonic shampoos" or the like, have been used mainly by male consumers. The tonic shampoos such as those containing menthol as the skin sensation inducing aromatic chemical can give sufficient refreshing feel, but because of their intense specific odor ascribed to the skin sensation inducing aromatic chemical, they have not been cared for by some consumers and especially by female consumers, and thus have had a quite limited market. Further, the specific or inherent odor of the aromatic chemical has made it difficult to impart a variety of fragrances to the shampoo compositions by ordinary mixed purfumes.

When the incorporation amount of the skin sensation inducing aromatic chemical such as menthol is reduced, the specific odor thereof can be mitigated but with only insufficient pharmaceutical effect. In order to obtain a certain pharmaceutical effect by a small incorporation of the chemical, a so-called percutaneous absorption accelerator could be used. However, among safe and economic materials, no adequate accelerator is known for enhancing the percutaneous absorption during only a temporary contact when the hair is shampooed. In turn, another approach has been made on odorless or less odoriferous external agents such as skin sensation inducing chemicals, but those giving sufficient effect and also safe to the human body have not yet been developed.

SUMMARY OF THE INVENTION

In order to overcome the above problems, the present inventors have made intensive studies and have found that when a skin sensation inducing aromatic chemical treated in advance by a modified cyclodextrin represented by the following formula (I) or (II):

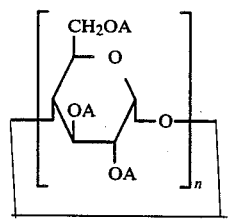

(I)

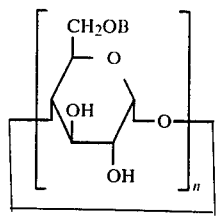

(II)

in which n represents a number from 6 to 9, A represents a hydrogen atom or a methyl group, and B represents a hydrogen atom or the group (III)

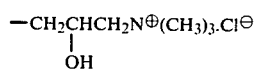

(III)

with the proviso that neither an ether substitution number of methyl group nor a substitution number of group (III) is less than 1,
is incorporated in a conventional shampoo composition, the specific odor of the skin sensation inducing aromatic chemical is effectively depressed, and that when urea is further incorporated thereto, more enhanced pharmaceutical effect is obtained. This invention is accomplished based on the above findings.

Accordingly, this invention provides a first invention which relates to a liquid shampoo composition comprising the following three components (A), (B) and (C):

(A) 5 to 30 wt% of at least one surface active agent,
(B) 0.05 to 5 wt% of a skin sensation inducing aromatic chemical, and
(C) ½ to twenty times by weight based on the amount of component (B) of a modified cyclodextrin represented by formula (I) or (II), and a second invention which relates to a liquid shampoo composition further comprising the component (D):

(D) 3 to 20 wt% of urea.

DETAILED DESCRIPTION OF THE INVENTION AND PREFERRED EMBODIMENTS

Hitherto, cyclodextrin is known to form an inclusion compound with various substances. For instance, it forms an inclusion compound with menthol at a molar ratio of about 1:1. Japanese patent application laid-open to the public No. 71132/1974 makes use of this and discloses a method of depressing the specific odor of antiphlogistic anodyne agents such as menthol, camphor and salicylic acid in poultices. In the compositions of the above publication, the odor of the odoriferous substances is mitigated because an inclusion compound is formed between the odoriferous substance and cyclodextrin. However, at the same time, the percutaneous absorption of the odoriferous substance is also depressed. This percutaneous absorption depressing action is utilized, for example, in Japanese patent publication No. 10323/1984, in which an inclusion compound is formed between a perfume and cyclodextrin in order to mitigate the percutaneous absorption of the perfume thereby reducing the side effect of skin irritation causable from the perfume while making use of only the fragance of the perfume.

According to this invention, the modified cyclodextrin also has an ability to form an inclusion compound with various substances, like cyclodextrin. However, a skin sensation inducing aromatic chemical such as menthol which is incorporated into a shampoo composition as expected to produce its pharmaceutical effect when absorbed into the head skin cannot achieve the main purpose if the percutaneous absorption is depressed. Accordingly, it has been admitted that, from the theoretical aspect, the pharmaceutical effect of the skin sensation inducing aromatic chemical can hardly be expected when an inclusion compound with cyclodextrin is incorporated into a shampoo composition.

It is true that once menthol, a skin sensation inducing aromatic chemical, is processed to form an inclusion compound with a modified cyclodextrin, the inherent refreshing feel of menthol can hardly be perceived when a diluted solution of the inclusion compound is applied to the scalp. However, the present inventors have noticed a singular phenomenon which had never been expected in that, when menthol treated by a modified cyclodextrin is incorporated into a shampoo composition, the specific odor of menthol is mitigated, and, sufficient refreshing or cool feel can be obtained when the shampoo composition is diluted by water and is applied to the head as the hair is washed or rinsed. Further, they have also found that a shampoo composition which incorporates the inventive inclusion compound has improved stability at low temperatures, because the inclusion compound between the skin sensation inducing aromatic chemical and a modified cyclodextrin is hardly settle at low temperatures. Although the detailed mechanism of the phenomenon is not made clear, it is reckoned that the three of a skin sensation inducing aromatic chemical, a modified cyclodextrin and a surface active agent form a complex in the presence of an excessive amount of the surface active agent, followed by being destroyed by a diluting operation, and thus the refreshing feel is revealed.

The surface active agents (A) usable as a base of the shampoo compositions according to the present invention include anionic surface active agents, nonionic surface active agents, amphoteric surface active agents and cationic surface active agents which follows:

Anionic surface active agents (1) Linear or branched alkylbenzenesulfonates having an alkyl group containing from 10 to 16 carbon atoms on average.

(2) Alkyl or alkenyl ether sulfates which have a linear or branched alkyl or alkenyl group containing from 10 to 20 carbon atoms on average and which are added with from 0.5 to 8 moles on average of ethylene oxide, propylene oxide, butylene oxide, from 0.1/9.9 to 9.9/0.1 of ethylene oxide / propylene oxide, or 0.1/9.9 to 9.9/0.1 of ethylene oxide / propylene oxide in one molecule.

(3) Alkyl- or alkenyl- sulfates having an alkyl or alkenyl group containing from 10 to 20 carbon atoms on average.

(4) Olefin sulfonates having from 10 to 20 carbon atoms on average in one molecule.

(5) Alkanesulfonates having from 10 to 20 carbon atoms on average in one molecule.

(6) Saturated or unsaturated fatty acid salts having from 10 to 24 carbon atoms on average in one molecule.

(7) Alkyl- or alkenyl- ether carboxylates which have an alkyl or alkenyl group containing from 10 to 20 carbon atoms on average and which are added with 0.5 to 8 moles of ethylene oxide, propylene oxide, butylene oxide, from 0.1/9.9 to 9.9/0.1 of ethylene oxide /propylene oxide, or 0.1/9.9 to 9.9/0.1 of ethylene oxide / propylene oxide in one molecule.

(8) Alpha-sulfo fatty acids or their esters having an alkyl or alkenyl group containing from 10 to 20 carbon atoms on average.

(9) N-acyl amino acid type surface active agents having an acyl group and a free carboxylic acid residue containing from 8 to 24 carbon atoms.

(10) Phosphoric mono- or di- ester type surface active agents having an alkyl or alkenyl group containing from 8 to 24 carbon atoms.

Amphoteric Surface Active Agents:

(11) Alpha-position addition type, secondary amide type, or tertiary amide type imidazoline amphoteric surface active agents having an acyl group containing carbon atoms from 8 to 24.

(12) Carbobetaine type, amidobetaine type, sulfobetaine type, hydroxy sulfobetaine type or amidosulfobetaine type amphoteric surface active agents having an alkyl, alkenyl or acyl group containing carbon atoms from 8 to 24.

Non-ionic Surface Active Agents:

(13) Polyoxyethylene alkyl or alkenyl ethers having an alkyl or alkenyl group containing from 10 to 20 carbon atoms on average and added with 1 to 20 mol ethylene oxide.

(14) Polyoxyethylene alkylphenyl ethers having an alkyl group containing from 6 to 12 carbon atoms on average and added with 1 to 20 mol ethylene oxide.

(15) Polyoxypropylene alkyl or alkenyl ethers having an alkyl or alkenyl group containing 10 to 20 carbon atoms on average and added with 1 to 20 mol prolylene oxide.

(16) Polyoxybutylene alkyl or alkenyl ethers having an alkyl or alkenyl group containing 10 to 20 carbon atoms on average and added with 1 to 20 mol butylene oxide.

(17) Nonionic active agents having an alkyl or alkenyl group containing 10 to 20 carbon atoms on average and added with 1 to 30 moles, in total, of ethylene oxide and propylene oxide or ethylene oxide and butylene oxide (a ratio of ethylene oxide and propylene oxide or butylene oxide is in the range of 0.1/9.9 to 9.9/0.1).

(18) Higher fatty acid alkanolamides having a long chain acyl group containing from 10 to 20 carbon atoms, or alkylene oxide adducts thereof.

(19) Sucrose fatty acid esters obtainable from fatty acid having from 10 to 20 carbon atoms on average and sucrose.

(20) Fatty acid glycerine monoesters obtainable from fatty acid having from 10 to 20 carbon atoms on average and glycerine.

(21) Alkylamine oxides having an alkyl or alkenyl group containing from 10 to 20 carbon atoms.

Cationic Surface Active Agents:

(22) Mono- or di- long chain alkyl quaternary amonium salts having from 10 to 20 carbon atoms.

The counter ions of the anionic residues of the above surfactants generally include ions of alkali metals such as sodium, potassium and the like; alkaline earth metals such as calcium and magnesium; ammonium ion and alkanolamines having 1 to 3 alkanol groups having 2 or 3 carbon atoms such as, for example, monoethanolamine, diethanolamine, triethanolamine, triisopropanolamine and the like. The counter ions of the cationic residues generally include halogen ions such as chlorine, bromine and iodine; methosulfates; and saccharinate ions.

Of the above described surfactants, especially preferred ones as a main active agent are anionic surfactants of (2) alkylethersulfates, (3) alkylsulfates, (4) olefinsulfonates and the like. Preferable examples include sodium polyoxyethylene laurylether sulfates (2 to 3 mol ethylene oxide added on average), triethanolamine lauryl sulfates, sodium alphaolefinsulfonates (average carbon number: 12-14) and so on.

These surfactants are incorporated into the liquid shampoo composition according to the invention by 5 to 30 wt%, preperably 10 to 20 wt% in total.

Skin sensation inducing aromatic chemicals usable as component (B) of the invention include menthol, camphor, methyl salicylate, cineol, menthone, piperitone, borneol, beta-pinene, menthyl acetate, varylamide nonylate, and the like. Of these, menthol, camphor and piperitone are expecially preferred. For menthol, l-menthol, d,l-menthol or essential oils containing l-menthol as an active ingredient may be used, among which l-menthol is most preferred.

The skin sensation inducing aromatic chemicals are treated by a modified cyclodextrin in advance and incorporated into the shampoo composition so as to have a final concentration of 0.05 to 5 wt%, preferably 0.1 to 2 wt%. Menthol incorporated less than 0.05 wt% gives only insufficient refreshing feel while over 5 wt% incorporation leads to a too strong cool feel and difficulty of homogeneous blending. In case where the skin sensation inducing aromatic chemicals are in a solid state, it is preferred to dissolve them in a small amount of a suitable solvent, followed by treating by a modified cyclodextrin.

The modified cyclodextrins to be used as component (C) in this invention are represented by the aforementioned formula (I) or (II), among which, those in which $n=6$ are named modified alpha-cyclodextrin, $n=7$ are named modified beta-cyclodextrin and $n=8$ are named modified gamma-cyclodextrin. The inclusion compound formability differs depending upon the type of alpha, bata and gamma.

Of components (C), the methylated cyclodextrins represented by formula (I) is prepared by methylating a cyclodextrin. When cyclodextrin is methylated according to the usual manner using a methylating agent such as dimethyl sulfuric acid, a mixture of methylated compounds having hydroxyl group of the glucose residue methylated at the 6- position, 2-position and 3-position can be obtained in this order. In the general formula (I), the number of A substituted by a methyl group is called "ether substitution number" i ("i" stands for an interger of from 1 to 3n). The ratio of methylated cyclodextrin having an ether substitution number "i" is expressed by $Bi$ (%). The ether substitution degree (DS) can be represented by the following equation by using Bi, i and n.

$$DS = \Sigma Bi \times i / 100n$$

In the formula (I), it is necessary at least one A among 3n times appearances of A is a methyl group. For instance, when methylated beta-cyclodextrin of $n=7$ is used, the substitution degree exceeeds 0.14 (1/7).

Examples of a manufacturing process of some methylated cyclodextrins represented by formula (I) are disclosed in several references. For example, preparation of hexakis-(2,3,6-tri-0-methyl)-alpha-cyclodextrin is disclosed in Berichte, vol. 69, page 2041, 1936, and hexakis-(2,6-di-0-methyl)-alpha-cyclodextrin and heptakis-(2,6-di-0-methyl)-beta-cyclodextrin are disclosed in Tetrahedron, vol. 24, page 803, 1968, and heptakis-(3-0-methyl)-beta-cyclodextrin and heptakis-(2-0-methyl)-beta-cyclodextrin are disclosed in Stärke, vol. 28, page 226, 1976. These are commertially available from, for example, Toshin Chemical K.K.

Among the methylated cyclodextrins of formula (I), those of $n=7$ and having an ether subsitution degree of from 1.14 to 1.60 are preferred in view of inclusion ability and the solubility in water, of which, those comprising 50 wt% or more of a methylated cyclodextrin having an ether substitution degree of from 1.14 to 1.60 and ether substitution number of from 8 to 11 are especially preferred.

The modified cyclodextrins represented by formula (II) are called cationic cyclodextrins, among which, those in which $n=6$ are named cationic alpha-cyclodextrin, $n=7$ are named cationic beta-cyclodextrin and $n=8$ are named cationic gamma-cyclodextrin. The inclusion compound formability differs depending upon the type of alpha, bata and gamma. All of them have a deodorant effect and thus usable in this invention. However, in view of the inclusion compound formability with a skin sensation inducing aromatic chemical, cationic beta-cyclodextrins are most preferred.

Cationic cyclodextrins are prepared by cationizing a cyclodextrin as described in Japanese patent application laid-open to the public No. 58-210901.

These modified cyclodextrins are usable in amounts ½ to 20 times, preferably 1 to 10 times by weight based on the amount of skin sensation inducing aromatic chemical. Almost no deodorizing effect is recognized if the amount less than ½ by weight based on the amount of skin sensation inducing aromatic chemical is used, while excess amount over twenty times can no more enhance the deodorizing effect.

Methods for treating a skin sensation inducing aromatic chemical with a modified cyclodextrin include the saturation solution method in which the chemical is added to a saturated solution of the modified cyclodextrin, and the kneading method in which the modified cyclodextrin and the skin sensation inducing aromatic chemical are kneaded in a kneader along with a small amount of water.

Urea as component (D) is used in an amount of from 3 to 20 wt% as needed. Amount less than 3 wt% cannot produce the pharmaceutical effect enhancing effect. On the other hand, excess amount over 20 wt% is of no use because it can no more increase the pharmaceutical effect enhancing effect.

The shampoo compositions according to this invention may further comprise, other than the above-described components, any arbitrary ingredients ordinarily incorporated into shampoo compositions. Examples of them are solubilizers such as propylene glycol, glycerine; viscosity modifiers such as ethanol, inorganic salts, higher alcohols, hydroxymethylcellulose, hydroxyethylcellulose, hydroxypropyl cellulose, methylcellulose and the like; perfumes; colorants; ultraviolet ray absorbers; antioxidants; antidandruff agents; bactericides; preservatives and the like. The remainder, water as vehicle, is used in general by 50 to 90 wt%, preferably 60 to 80 wt%.

The present invention is described by way of synthetic examples and examples. Throughout the synthetic examples and the examples, "%" is on a weight basis. Data for the incorporation amount of the commertial surfactant products such as Miranol C2M Conc. are indicated by wt% of active ingredients.

SYNTHETIC EXAMPLE 1

Methylated beta-cyclodextrin:

113.5 g (0.1 mol) of beta-cyclodextrin (hereinafter may be referred to as "beta-CD") was suspended into 324.5 g (2.43 mol) of an aqueous 30% NaOH solution and agitated for 30 minutes at room temperature. Into the thus obtained mixture, 264.8 g (2.1 mol) of dimethyl sulfuric acid wa gradually dropped while the system was cooled with ice. After completion of the dropping, agitation was further carried out for 4 hours at 60° C., to which 100 ml of water was added, followed by 1 more hour agitation at 85° C.

The obtained reaction mixture was cooled down and extracted three times each with 300 ml of methylene chloride. The organic phase was taken and washed twice with 300 ml of water, further washed with 300 ml of saturated saline solution, dried over Glauber's salt, and the solvent was distilled off to obtain 74.1 g (yield: 57.1%) of methylated beta-CD in white crystal having an ether subsitution degree of 1.67.

The same procedures as above were repeated except that 190.3 g (1.51 mol) of dimethyl sulfuric acid was used while other materials and incorporation amont being unchanged to obtain a methylated beta-CD of a substitution degree of 1.2, and 44.4 g (0.35 mol) of dimethyl sulffuric acid was used to obtain a methylated beta-CD of a substitution degree of 0.28.

Synthetic Example 2

126.5 g of beta-CD (90% purity, 0.100 mol) and 149.5 g (1.12 mol) of an aqueous 30 wt% NaOH solution were charged in a reaction vessel, mixed and heated up to 30° C. The reaction system was in a state of white slurry. 120 g (0.95 mol) of dimethyl sulfuric acid was dropped over 2 hours while the vessel was cooled to maintain the temperature at 30° C. The reaction mixture was a yellow transparent liquid. After the completion of the dropping, the system was heated up to 40° C., and mixed well for 4 hours to complete the reaction. Thereafter, 15 g (0.11 mol) of an aqueous 30 wt% NaOH solution was added and mixed for 2 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 118 g of methylated beta-CD was obtained in a white powder.

Analysis by the high performance liquid chromatography (HPLC) revealed that the obtained methylated beta-CD had a composition shown in Table 1. Ether substitution degree was 1.14. Total of the weight % of each methylated beta-CD having an ether substitution number ranging from 8 to 11 was 58 wt%. The measurement conditions for HPLC were as follows:

Measurement Conditions:
Type of the Instrument:
  High Performance Liquid Chromatograph #665 (manufactured by Hitachi Seisakusho K.K.)
Detector:
  RI detector
Filler:
  Fine SIL NH$_2$
  particle size: 10 micrometers
  (manufactured by Nippon Bunko K.K.)
Column Size:
  4.6 mm$\phi \times$ 250 mm (L),
  2 columns connected
Elution liquid:
  Acetonitrile/Water =60/40

SYNTHETIC EXAMPLE 3 126.5 g of beta-CD (90% purity, 0.100 mol) and 472 g (1.77 mol) of an aqueous 15 wt% NaOH solution were charged in a reaction vessel and mixed. The reaction system was in a state of yellow transparent liquid. 189 3 g (1.50 mol) of dimethyl sulfuric acid was dropped over hours while the reaction system was cooled to maintain the temperature at 20° C.

The reaction mixture was yellow transparent liquid. After the completion of the dropping, the system was heated up to 40° C., and mixed well for 4 hours to complete the reaction. Thereafter, 47 g (0.18 mol) of an aqueous 15 wt% NaOH solution was added and mixed for 2 hours at 70° C., to which 98 wt% of sulfuric acid was added to adjust the pH to 7 for neutralization.

Then, electro-dialysis was carried out to remove sodium methylsulfate and sodium sulfate. When the desalted solution was freeze-dried, 122 g of methylated beta-CD was obtained in a white powder.

Analysis by the high performance liquid chromatography (HPLC) revealed that the obtained methylated beta-CD had a composition shown in Table 1. Ether substitution degree was 1.29. Total of the weight % of each methylated beta-CD having an ether substitution number ranging from 8 to 11 was 69 wt%. The measurement conditions for HPLC were the same as in Synthetic Example 2.

SYNTHETIC EXAMPLE 4

126.5 g of beta-CD (90% purity, 0.100 mol) and 552 g (2.07 mol) of an aqueous 15 wt% NaOH solution were charged in a reaction vessel and mixed. The reaction system was in a state of yellow transparent liquid. 220.5 g (1.75 mol) of dimethyl sulfuric acid was dropped over 4 hours while the reaction system was cooled to maintain the temperature at 20° C. The reaction mixture was a yellow transparent liquid. After the completion of the dropping, the system was heated up to 40° C., and mixed well for 4 hours to complete the reaction. Thereafter, 55 g (0.21 mol) of an aqueous 15 wt% NaOH solution was added and mixed for 2 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 123 g of methylated beta-CD was obtained in a white powder.

Analysis by the high performance liquid chromatography (HPLC) revealed that the obtained methylated beta-CD had a composition shown in Table 1. Ether substitution degree was 1.34. Total of the weight of each methylated beta-CD having an ether substitution number ranging from 8 to 11 was 77 wt%. The measurement conditions for HPLC were the same as in Synthetic Example 2.

SYNTHETIC EXAMPLE 5

126.5 g of beta-CD (90% purity, 0.100 mol) and 331 g (2.48 mol) of an aqueous 30 wt% NaOH solution were charged in a reaction vessel, mixed and heated up to 30° C. The reaction system was in a state of white slurry. 265 g (2.10 mol) of dimethyl sulfuric acid was dropped over 5 hours while the vessel was cooled to maintain the temperature at 30° C. The reaction mixture was yellow transparent liquid. After the completion of the dropping, the system was heated up to 40° C., and mixed well for 4 hours to complete the reaction. Thereafter, 33.1 g (0.25 mol) of an aqueous 30 wt% NaOH solution was added and mixed for 2 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 125 g of methylated beta-CD was obtained in a white powder.

Analysis by the high performance liquid chromatography (HPLC) revealed that the obtained methylated beta-CD had a composition shown in Table 1. Ether substituion degree was 1.56. Total of the weight of each methylated beta-CD having an ether substitution number ranging from 8 to 11 was 52 wt%. The measurement conditions for HPLC were the same as in Synthetic Example 2.

SYNTHETIC EXAMPLE 6

126.5 g of beta-CD (90% purity, 0.100 mol) and 472 g (1.77 mol) of an aqueous 15 wt% NaOH solution were charged in a reaction vessel and mixed. The reaction system was in a state of yellow transparent liquid. 189 g (1.50 mol) of dimethyl sulfuric acid was dropped over 3 hours while the reaction vessel was cooled to maintain the temperature at 60° C. The reaction mixture was a yellow transparent liquid. After the completion of the dropping, the system was further agitated for 1 hour by maintaining the temperature of the system at 60° C. to complete the reaction. Thereafter, 47 g (0.18 mol) of an aqueous 15 wt% of NaOH solution was added and mixed for 2 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 119 g of methylated beta-CD was obtained in a white powder.

Analysis by the high performance liquid chromatography (HPLC) revealed that the obtained methylated beta-CD had a composition shown in Table 1. Ether substitution degree was 1.20. Total of the weight of each methylated beta-CD having an ether substituion number ranging from 8 to 11 was 63 wt%. The measurement conditions for HPLC were the same as in Synthetic Example 2.

SYNTHETIC EXAMPLE 7

126.5 g of beta-CD (90% purity, 0.100 mol) and 95.2 g (0.714 mol) of an aqueous 30 wt% NaOH solution were charged in a reaction vessel, mixed and heated up to 30° C. The reaction system was in a state of white slurry. 75.7 g (0.600 mol) of dimethyl sulfuric acid was dropped over 2 hours while the vessel was cooled to maintain the temperature at 30° C. The reaction mixture was a yellow transparent liquid. After the completion of the dropping, the system was heated up to 40° C., and mixed well for 4 hours to complete the reaction. Thereafter, 9.5 g (0.07 mol) of an aqueous 30 wt% of NaOH solution was added and mixed for 4 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 112 g of methylated beta-CD was obtained in a white powder.

Analysis by the high performance liquid chromatography (HPLC) revealed that the obtained methylated beta-CD had a composition shown in Table 1. Ether substitution degree was 0.70. Total of the weight of each methylated beta-CD having an ether substitution number ranging from 8 to 11 was 26 wt%. The measurement conditions for HPLC were the same as in Synthetic Example 2.

SYNTHETIC EXAMPLE 8

126.5 g of beta-CD (90% purity, 0.100 mol) and 114.2 g (0.857 mol) of an aqueous 30 wt% NaOH solution were charged in a reaction vessel, mixed and heated up to 30° C. The reaction system was in a state of white slurry. 90.8 g (0.720 mol) of dimethyl sulfuric acid was dropped over 2 hours while the vessel was cooled to maintain the temperature at 30° C. The reaction mixture was a yellow transparent liquid. After the completion of the dropping, the system was heated up to 40° C., and mixed well for 4 hours to complete the reaction. Thereafter, 11.4 g (0.086 mol) of an aqueous 30 wt% NaOH solution was added and mixed for 4 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 114 g of methylated beta-CD was obtained in a white powder.

Analysis by the high performance liquid chromatography (HPLC) revealed that the obtained methylated beta-CD had a composition shown in Table 1. Ether substitution degree was 0.91. Total of the weight % of each methylated beta-CD having an ether substitution number ranging from 8 to 11 was 27 wt%. The measurement conditions for HPLC were the same as in Synthetic Example 2.

SYNTHETIC EXAMPLE 9

126.5 g of beta-CD (90% purity, 0.100 mol) and 550.7 g (4.13 mol) of an aqueous 30 wt% NaOH solution were charged in a reaction vessel, mixed and heated up to 30° C. The reaction system was in a state of white slurry. 441.5 g (3.50 mol) of dimethyl sulfuric acid was dropped over 2 hours while the vessel was cooled to maintain the temperature at 30° C. The reaction mixture was a yellow transparent liquid. After the completion of the dropping, the system was heated up to 40° C., and mixed well for 4 hours to complete the reaction. Thereafter, 55.1 g (0.41 mol) of an aqueous 30 wt% NaOH solution was added and mixed for 4 hours at 70° C., to which 98 wt% of sulfuric acid was added to adjust the pH to 7 for neutralization. Then, electro-dialysis was carried out to remove sodium methylsulfate and sodium sulfate. When the desalted solution was freeze-dried, 125 g of methylated beta-CD was obtained in a white powder.

Analysis by the high performance liquid chromatography (HPLC) revealed that the obtained methylated beta-CD had a composition shown in Table 1. Ether substitution degree was found to be 1.66. Total of the weight % of each methylated beta-CD having an ether substitution number ranging from 8 to 11 was 40 wt%. The measurement conditions for HPLC were the same as in Synthetic Example 2.

TABLE 1

|  |  | Composition of Methylated Beta-CD | | | | | | | |
|---|---|---|---|---|---|---|---|---|---|
|  |  | Synthetic Example 2 | Synthetic Example 3 | Synthetic Example 4 | Synthetic Example 5 | Synthetic Example 6 | Synthetic Example 7 | Synthetic Example 8 | Synthetic Example 9 |
| Ether Substitution Degree |  | 1.14 | 1.29 | 1.34 | 1.56 | 1.20 | 0.70 | 0.91 | 1.66 |
| Composition (%) | β-CD | 0 | 0 | 0 | 0 | 0 | 11 | 0 | 0 |
| Ether Substitution Number | 1 | 0 | 0 | 0 | 0 | 0 | 10 | 0 | 0 |
|  | 2 | 0 | 0 | 0 | 0 | 0 | 7 | 1 | 0 |
|  | 3 | 1 | 0 | 0 | 0 | 1 | 7 | 4 | 0 |
|  | 4 | 3 | 1 | 0 | 0 | 2 | 7 | 10 | 0 |
|  | 5 | 7 | 3 | 1 | 0 | 5 | 9 | 17 | 0 |
|  | 6 | 12 | 7 | 4 | 1 | 9 | 11 | 21 | 0 |
|  | 7 | 17 | 11 | 8 | 3 | 14 | 12 | 20 | 0 |
|  | 8 | 20 | 17 | 15 | 6 | 18 | 11 | 15 | 2 |
|  | 9 | 17 | 19 | 21 | 11 | 18 | 8 | 8 | 6 |
|  | 10 | 11 | 19 | 23 | 16 | 15 | 5 | 3 | 12 |
|  | 11 | 10 | 14 | 18 | 19 | 12 | 2 | 1 | 20 |
|  | 12 | 2 | 9 | 10 | 21 | 6 | 0 | 0 | 27 |
|  | 13 | 0 | 0 | 0 | 23 | 0 | 0 | 0 | 33 |
|  | 14 | 0 | 0 | 0 | 0 | 0 | 0 | 0 | 0 |

EXAMPLE 1

Shampoo compositions shown in Table 2 were prepared by the usual manner. When both of menthol and cationic cyclodextrin were incorporated at the same time, an inclusion compound thereof was prepared in advance by the saturated solution method, and the obtained inclusion compound was incorporated into the shampoo compositions so that the final compositions have the concentrations indicated in Table 2.

Menthol odor of non-diluted compositions obtained above and refreshing feel of the compositions diluted by 10 times of water were evaluated according to the following criteria, respectively. The results are shown in Table 2.

(1) Menthol Odor:
The menthol odor of each non-diluted liquid composition was evaluated according to the following criteria by a perfumer.
◎ : no menthol odor
○ : very slight menthol odor
Δ: weak menthol odor
X: definite menthol odor
XX: strong menthol odor (2) Refreshing Feel:
10 microliters of each sample liquid was applied to an adhesive plaster for patch test. The plaster was applied to the neck of ten panelists. The refreshing feel was evaluated according to the following criteria.
1: no refreshing feel
2: slight refreshing feel
3: definite refreshing feel
4: strong refreshing feel
5: too strong refreshing feel to continue the application of the plaster

TABLE 2

| Formulation | Inventive Composition | | | | | Comparative Composition | | | | | |
|---|---|---|---|---|---|---|---|---|---|---|---|
|  | (1) | (2) | (3) | (4) | (5) | (1) | (2) | (3) | (4) | (5) | (6) |
| Sodium laurylsulfate | 20 |  |  |  |  | 20 |  |  |  |  |  |
| Sodium polyoxyethylene(2.5)laurylether sulfate |  | 20 |  |  |  |  | 20 |  |  |  |  |
| Imidazoline-type amphoteric surface active agent* |  |  | 20 |  |  |  |  | 20 |  |  |  |
| Cetyltrimethylammonium chloride |  |  |  | 20 |  |  |  |  | 20 |  |  |
| Polyoxyethylene(10)laurylether |  |  |  |  | 20 |  |  |  |  | 20 |  |
| Cationic beta-cyclodextrin** | 1 | 1 | 1 | 1 | 1 |  |  |  |  |  | 1 |
| l-Menthol | 0.2 | 0.2 | 0.2 | 0.2 | 0.2 | 0.2 | 0.2 | 0.2 | 0.2 | 0.2 | 0.2 |
| Ion exchanged water | 78.8 | 78.8 | 78.8 | 78.8 | 78.8 | 79.8 | 79.8 | 79.8 | 79.8 | 79.8 | 79.8 |
| Menthol Odor of non-diluted composition | ◎ | ◎ | ◎ | ◎ | ◎ | x | x | x | x | x | ◎ |
| Refreshing feel of composition diluted by 10 times of water | 3 | 3 | 3 | 3 | 3 | 3 | 3 | 3 | 3 | 3 | 1 |

*Miranol C2M Conc. by Miranol Corp.
**Cationic beta-cyclodextrin of formula (II) used in from Example 1 to Example 7 are prepared in the same manner as Example 1 in Japanese Patent Application Laid Open No. 210901/1983, in which n = 7 and among n times appearance of B, 2.7 on average of B's represent —CH$_2$CHCH$_2$N$^\oplus$(CH$_3$)$_3$ · Cl$^\ominus$.
　　|
　　OH

EXAMPLE 2

Shampoo compositions shown in Table 3 were prepared in the usual manner. Menthol odor and refreshing feel of the compositions were evaluated by the same manner as in Example 1. The results are shown in Table 3.

TABLE 3

| Formulation | Inventive Composition | | | | | | | Comparative Composition | | | |
|---|---|---|---|---|---|---|---|---|---|---|---|
|  | (6) | (7) | (8) | (9) | (10) | (11) | (12) | (7) | (8) | (9) | (10) |
| Triethanolamine laurylsulfate | 16 | 16 | 16 | 16 | 16 | 16 | 16 | 16 | 16 | 16 | 16 |
| Coconut fatty acid diethanolamide | 3 | 3 | 3 | 3 | 3 | 3 | 3 | 3 | 3 | 3 | 3 |
| Cationic alpha-cyclodextrin*** |  |  |  |  |  | 2 |  |  |  |  |  |
| Cationic beta-cyclodextrin | 10 | 5 | 2 | 1 | 0.2 |  |  | 0.2 |  |  |  |

TABLE 3-continued

| Formulation | Inventive Composition | | | | | | | Comparative Composition | | | |
|---|---|---|---|---|---|---|---|---|---|---|---|
| | (6) | (7) | (8) | (9) | (10) | (11) | (12) | (7) | (8) | (9) | (10) |
| Cationic gamma-cyclodextrin**** | | | | | | | 2 | | | | |
| l-Menthol | 1 | 0.5 | 0.2 | 0.2 | 0.2 | 0.2 | 0.2 | 1 | 1 | 0.5 | 0.2 |
| Ion exchanged water | 70 | 75.5 | 78.8 | 79.8 | 80.6 | 78.8 | 78.8 | 79.8 | 80 | 80.5 | 80.8 |
| Menthol odor of non-diluted composition | ⊚ | ⊚ | ⊚ | ⊚ | ⊚ | ○ | ○ | xx | xx | xx | x |
| Refreshing feel of composition diluted by 10 times of water | 5 | 4 | 3 | 3 | 3 | 3 | 3 | 5 | 5 | 4 | 3 |

***Cationic alpha-cyclodextrin (in formula (II), n represents 6, substitution degree is 2.3 (average))
****Cationic gamma-cyclodextrin (in formula (II), n represents 8, substitution degree is 3.1 (average))

EXAMPLE 3

Shampoo composition having the following formulations were prepared. The panelists used the two shampoo compositions, applying one composition to the left side and the other to the right side of the head, and washed the hair. Refreshing feel of the compositions was compared with each other. As a result, no difference in the refreshing feel was found between the two compositions.

| | Inventive Composition (13) | Comparative Composition (11) |
|---|---|---|
| Sodium polyoxyethylene (2.5) laurylether sulfate | 16 | 16 |
| Coconut fatty acid diethanolamide | 3 | 3 |
| Sodium chloride | 0.2 | 0.2 |
| Perfume | 0.4 | 0.4 |
| Cationic beta-cyclodextrin | 0.3 | — |
| l-Menthol | 0.2 | 0.2 |
| Sodium benzoate | 0.5 | 0.5 |
| Water | 79.4 | 79.7 |

EXAMPLE 4

Shampoo compositions having the following formulations were prepared. Menthol odor of each composition was evaluated by 10 panelists. The results are shown in Table 4.

| | Inventive Composition (14) | Comparative Composition (12) |
|---|---|---|
| Triethanolamine lauryl sulfate | 12 | 12 |
| Lauric acid diethanolamine | 5 | 5 |
| Methylcellulose | 0.5 | 0.5 |
| Methylperaben | 0.5 | 0.5 |
| Cationic beta-cyclodextrin | 1 | — |
| Menthol | 0.2 | 0.2 |
| Perfume | 0.6 | 0.6 |
| Water | 80.2 | 81.2 |

TABLE 4

| | Menthol Odor | | |
|---|---|---|---|
| | none | slight | perceived |
| Inventive Composition (14) | 8 | 2 | 0 |
| Comparative Composition (12) | 3 | 5 | 2 |

EXAMPLE 5

Shampoo compositions shown in Table 5 were prepared. Menthol odor and refreshing feel of the compositions were evaluated by the same manner as in Example 1. The results are shown in Table 5.

TABLE 5

| Formulation | Inventive Composition | | | | |
|---|---|---|---|---|---|
| | (15) | (16) | (17) | (18) | (19) |
| Sodium laurylsulfate | 20 | 20 | 20 | 20 | 20 |
| Coconut fatty acid diethanolamide | 3 | 3 | 3 | 3 | 3 |
| l-Menthol | 0.2 | 0.2 | 0.2 | 0.2 | 0.2 |
| Urea | 3 | 6 | 10 | 0 | 1 |
| Cationic beta-cyclodextrin | 1 | 1 | 1 | 1 | 1 |
| Ion exchanged water | 72.8 | 69.8 | 65.8 | 75.8 | 74.8 |
| Menthol odor of non-diluted composition | ⊚ | ⊚ | ⊚ | ⊚ | ⊚ |
| Refreshing feel of composition diluted by 10 times of water | 4 | 5 | 5 | 3 | 3 |

EXAMPLE 6

A transparent tonic shampoo composition having the following formulation containing an antidandruff agent (pyroctonauramine) was prepared.

| | Inventive Composition (20) |
|---|---|
| Sodium polyoxyethylene (2.5) laurylether sulfate | 14 |
| Lauryldimethylamine oxide | 5 |
| Imidazoline-type amphoteric surface active agent (Miranol C2M Conc.) | 1 |
| l-Menthol | 1 |
| Cationic beta-cyclodextrin | 10 |
| Pyroctonauramine (Octpyrox: Henkel Corp.) | 1 |
| Ion exchanged water | 68 |

EXAMPLE 7

Menthol treated by cyclodextrins of a kind and an amount shown in Table 6 were incorporated in a shampoo composition having the folowing formulation.

Triethanolamine laurylsulfate: 16 (wt %)
Lauric acid diethanolamide: 3
Perfume: 0.4
Cyclodextrins: (see Table 6)
Menthol: 0.2
Methylcellulose: 0.5
Water: balance After storing the compositions at −5° C. for one month, the stability of each composition was examined. The results are shown in Table 6.

TABLE 6

| Component | Incorporated Amount (wt %) | Stability at Low Temp.* |
|---|---|---|
| Beta-cyclodextrin | 0.1 | O |
|  | 0.3 | O |
|  | 0.5 | X |
|  | 0.7 | X |
|  | 1.0 | X |
|  | 2.0 | X |
| Cationic Beta-cyclodextrin | 0.1 | O |
|  | 0.3 | O |
|  | 0.5 | O |
|  | 0.7 | O |
|  | 1.0 | O |
|  | 2.0 | O |

*: O - transparent, X - opaque or precipitated

EXAMPLE 8

Shampoo compositions shown in Table 7 were prepared by the usual manner. When both of menthol and methylated cyclodextrin were incorporated at the same time, an inclusion compound thereof was prepared in advance by the saturated solution method and the obtained inclusion compounds were incorporated into the shampoo compositions so that the final compositions have the concentrations indicated in Table 7.

Menthol odor of non-diluted compositions obtained above and refreshing feel of the compositions diluted by 10 times of water were evaluated according to the criteria adopted in Example 1, respectively. The results are shown in Table 7.

TABLE 7

| Formulation | Inventive Composition | | | | | Comparative Composition | | | | | |
|---|---|---|---|---|---|---|---|---|---|---|---|
|  | (20) | (21) | (22) | (23) | (24) | (13) | (14) | (15) | (16) | (17) | (18) |
| Sodium laurylsulfate | 20 |  |  |  |  | 20 |  |  |  |  |  |
| Sodium polyoxyethylene (2.5) laurylether sulfate |  | 20 |  |  |  |  | 20 |  |  |  |  |
| Imidazoline-type amphoteric surface active agent* |  |  | 20 |  |  |  |  | 20 |  |  |  |
| Cetyltrimethylammoniumchloride |  |  |  | 20 |  |  |  |  | 20 |  |  |
| Polyoxyethylene(10)laurylether |  |  |  |  | 20 |  |  |  |  | 20 |  |
| Methylated beta-cyclodextrin (Ether substitution degree = 1.2)** | 1 | 1 | 1 | 1 | 1 |  |  |  |  |  | 1 |
| l-menthol | 0.2 | 0.2 | 0.2 | 0.2 | 0.2 | 0.2 | 0.2 | 0.2 | 0.2 | 0.2 | 0.2 |
| Ion exchanged water | 78.8 | 78.8 | 78.8 | 78.8 | 78.8 | 79.8 | 79.8 | 79.8 | 79.8 | 79.8 | 79.8 |
| Menthol odor of non-diluted composition | ⊚ | ⊚ | ⊚ | ⊚ | ⊚ | x | x | x | x | x | O |
| Refreshing feel of composition diluted by 10 times of water | 3 | 3 | 3 | 3 | 3 | 3 | 3 | 3 | 3 | 3 | 1 |

*Miranol C2M Conc. by Miranol Corp.
**Gullucose: Among 3 A's, the member of A's which are substituted into methyl are 1.2 on average (Synthetic Example 1).

EXAMPLE 9

Shampoo compositions shown in Table 8 were prepared in the usual manner. Menthol odor and refreshing feel of the compositions were evaluated by the same manner as in Example 1. The results are shown in Table 8.

TABLE 8

| Formulation | Inventive Composition | | | | | | | | | Comparative Composition | | | |
|---|---|---|---|---|---|---|---|---|---|---|---|---|---|
|  | (25) | (26) | (27) | (28) | (29) | (30) | (31) | (32) | (33) | (19) | (20) | (21) | (22) |
| Triethanolamine laurylsulfate | 16 | 16 | 16 | 16 | 16 | 16 | 16 | 16 | 16 | 16 | 16 | 16 | 16 |
| Coconut fatty acid diethanolamide | 3 | 3 | 3 | 3 | 3 | 3 | 3 | 3 | 3 | 3 | 3 | 3 | 3 |
| Methylated β-cyclodextrin (Ether substitution degree = 1.2)* | 10 | 5 | 2 | 1 | 0.2 |  |  |  |  | 0.2 |  |  |  |
| Methylated β-cyclodextrin (Ether substitution degree = 0.28)* |  |  |  |  |  | 2 |  |  |  |  |  |  |  |
| Methylated β-cyclodextrin (Ether substitution degree = 1.67)* |  |  |  |  |  |  | 2 |  |  |  |  |  |  |
| Heptakis-(2,6-di-O—methyl)-β-cyclodextrin** |  |  |  |  |  |  |  | 2 |  |  |  |  |  |
| Heptakis-(2,3,6-tri-O—methyl)-β-cyclodextrin** |  |  |  |  |  |  |  |  | 2 |  |  |  |  |
| l-Menthol | 1 | 0.5 | 0.2 | 0.2 | 0.2 | 0.2 | 0.2 | 0.2 | 0.2 | 1 | 1 | 0.5 | 0.2 |
| Ion exchanged water | 70 | 75.5 | 78.8 | 79.8 | 80.6 | 78.8 | 78.8 | 78.8 | 78.8 | 79.8 | 80 | 80.5 | 80.8 |
| Menthol odor of non-diluted composition | ⊚ | ⊚ | ⊚ | ⊚ | ⊚ | ⊚ | ⊚ | ⊚ | ⊚ | xx | xx | xx | x |
| Refreshing feel of composition diluted by 10 times of water | 5 | 4 | 3 | 3 | 3 | 3 | 3 | 3 | 3 | 5 | 5 | 4 | 3 |

*Synthetic Example 1
**Product of Toshin Chemical Corp.

EXAMPLE 10

Shampoo compositions having the following formulations were prepared. Ten panelists used the two shampoo compositions, applying one composition to the left side and the other to the right side of the head, and washed the hair. Refreshing feel of the compositions was compared with each other. As a result, no difference in the refreshing feel was found between the two compositions.

| | Inventive Composition (34) | Comparative Composition (23) |
|---|---|---|
| Sodium polyoxyethylene (2.5) laurylether sulfate | 16 | 16 |
| Coconut fatty acid diethanolamide | 3 | 3 |
| Sodium chloride | 0.2 | 0.2 |
| Perfume | 0.4 | 0.4 |
| Methylated beta-cyclodextrin (ether substitution degree = 1.2) | 0.3 | — |
| Menthol | 0.2 | 0.2 |
| Sodium benzoate | 0.5 | 0.5 |
| Water | 79.4 | 79.7 |

EXAMPLE 11

Shampoo compositions having the following formulations were prepared. Presence of menthol odor in the compositions obtained was checked by ten panelists. The results are shown in Table 9.

| | Inventive Composition (35) | Comparative Composition (24) |
|---|---|---|
| Triethanolamine laurylsulfate | 12 | 12 |
| Lauric acid diethanolamide | 5 | 5 |
| Methylcellulose | 0.5 | 0.5 |
| Methylperaben | 0.5 | 0.5 |
| Methylated beta-cyclodextrin (ether substitution degree = 1.2) | 1 | — |
| Menthol | 0.2 | 0.2 |
| Perfume | 0.6 | 0.6 |
| Water | 80.2 | 81.2 |

TABLE 9

| | Menthol Odor | | |
|---|---|---|---|
| | none | slight | perceived |
| Inventive Composition (35) | 8 | 2 | 0 |
| Comparative Composition (24) | 3 | 5 | 2 |

EXAMPLE 12

Shampoo compositions shown in Example 10 were prepared and menthol odor and refreshing feel of the compositions were evaluated in the same manner as in Example 1. The results are shown in Table 10.

TABLE 10

| Formulation | Inventive Composition | | | | |
|---|---|---|---|---|---|
| | (36) | (37) | (38) | (39) | (40) |
| Sodium laurylsulfate | 20 | 20 | 20 | 20 | 20 |
| Coconut fatty acid diethanolamide | 3 | 3 | 3 | 3 | 3 |
| l-Menthol | 0.2 | 0.2 | 0.2 | 0.2 | 0.2 |
| Urea | 3 | 6 | 10 | 0 | 1 |
| Methylated beta-cyclodextrin (Ether substitution degree = 1.2) | 1 | 1 | 1 | 1 | 1 |
| Ion exchanged water | 72.8 | 69.8 | 65.8 | 75.8 | 74.8 |

TABLE 10-continued

| Formulation | Inventive Composition | | | | |
|---|---|---|---|---|---|
| | (36) | (37) | (38) | (39) | (40) |
| Menthol odor of non-diluted composition | ◎ | ◎ | ◎ | ◎ | ◎ |
| Refreshing feel of composition diluted by 10 times of water | 4 | 5 | 5 | 3 | 3 |

EXAMPLE 13

A transparent tonic shampoo composition having the following formulation containing an antidandruff agent (pyroctonauramine) was prepared.

| | Inventive Composition (41) |
|---|---|
| Sodium polyoxyethylene(2.5)lauryl-ether sulfate | 14 |
| Lauryldimethylamine oxide | 5 |
| Imidazoline-type amphoteric surface active agent (Miranol C2M Conc.) | 1 |
| l-Menthol | 1 |
| Methylated beta-cyclodextrin (ether substitution degree = 1.2) | 10 |
| Pyroctonauramine (Octpyrox: Henkel Corp.) | 1 |
| Ion exchanged water | 68 |

EXAMPLE 14

Menthol treated by cyclodextrins of a kind and an amount indicated in Table 11 is incorporated in a shampoo composition having the following formulation.

Triethanolamine laurylsulfate: 16 (wt %)
Lauric acid diethanolamide: 3
Perfume: 0.4
Cyclodextrins: (see Table 11)
Menthol: 0.2
Methylcellulose: 0.5
Water: balance After storing the compositions at −5° C. for one month, the stability of each composition was examined. The results are shown Table 11.

TABLE 11

| | Stability at Low Temperature | | | | | |
|---|---|---|---|---|---|---|
| Component | Incorporated Amount (wt %) | | | | | |
| | 0.1 | 0.3 | 0.5 | 0.7 | 1.0 | 2.0 |
| Beta-cyclodextrin | O | O | X | X | X | X |
| Methylated beta-cyclodextrin (Ether substitution degree = 0.28) | O | O | O | O | O | O |
| Methylated beta-cyclodextrin (Ether substitution degree = 1.2) | O | O | O | O | O | O |
| Methylated beta-cyclodextrin (Ether substitution degree = 1.67) | O | O | O | O | O | O |
| Heptakis-(2,6-di-O—methyl)-beta-cyclodextrin | O | O | O | O | O | O |
| Heptakis-(2,3,6-tri-O—methyl)-beta-cyclodextrin | O | O | O | O | O | O |

O: Transparent
X: Opaque or Precipitated

EXAMPLE 15

Methylated beta-cyclodextrins obtained in Synthetic Examples 2 to 6 and Comparative Examples 1 to 3 and menthol were processed into inclusion compounds with a molar ratio of 1:1. The obtained compounds were incorporated into the shampoo composition having the following formulation so that 0.2 wt % of menthol was included in the composition. After spotting each shampoo composition to TLC, each spot was spread by a mixed solvent of hexane/ethylether (50/50). The thus treated shampoo compositions were collected by methanol as a sample, respectively. Thereafter, a dimethylaminobenzaldehyde sulfuric acid solution was dropped to each sample to obtain a coloration of menthol contained in the shampoo composition. The amount of menthol in the composition was determined from the absorbance at a wave length of 530 nm, and the inclusion degree was determined by the following calculation formula.

Inclusion Degree (%) =

$$\frac{\text{Amount of menthol reacted with methylated beta-CD to form a inclusion compound in sample}}{\text{Total amount of menthol in sample}} \times 100$$

[Formulation of Shampoo Composition]

| Triethanolamine laurylsulfate | 16 (wt %) |
|---|---|
| Coconut fatty acid diethanolamide | 3 |
| Methylated beta-CD included with l-menthol (m.w. = 156.3) | 0.2 (as l-menthol) |
| Ion exchanged water | balance |

[Results]

TABLE 12

| Composition No. | Methylated beta-CD which was incorporated | Inclusion degree |
|---|---|---|
| 41 | Obtained in Synthetic Example 2 | 76 |
| 42 | Obtained in Synthetic Example 3 | 83 |
| 43 | Obtained in Synthetic Example 4 | 81 |
| 44 | Obtained in Synthetic Example 5 | 79 |
| 45 | Obtained in Synthetic Example 6 | 85 |
| 46 | Obtained in Synthetic Example 7 | 69 |
| 47 | Obtained in Synthetic Example 8 | 68 |
| 48 | Obtained in Synthetic Example 9 | 72 |
| 49 | Beta-CD | 69 |

As shown in the above table, methylated beta-cyclodextrins of an ether substitution degree of 1.14–1.60 (obtained in Synthetic Examples 2 to 6) have a good inclusion ability.

EXAMPLE 16

Skin sensation inducing aromatic chemicals were treated by methylated cyclodextrin and then incorporated into the shampoo compositions shown in Table 13 according to the usual manner.

TABLE 13

| Formulation | Inventive Composition | | | | | | | |
|---|---|---|---|---|---|---|---|---|
| | 49 | 50 | 51 | 52 | 53 | 54 | 55 | 56 |
| Triethanolamine laurylsulfate | 16 | 16 | 16 | 16 | 16 | 16 | 16 | 16 |
| Coconut fatty acid diethanolamide | 3 | 3 | 3 | 3 | 3 | 3 | 3 | 3 |
| Skin sensation inducing aromatic chemical | | | | | | | | |
| Camphor | 0.2 | — | — | — | — | — | — | — |
| Methyl salicylate | — | 0.2 | — | — | — | — | — | — |
| Thymol | — | — | 0.2 | — | — | — | — | — |
| Pipertone | — | — | — | 0.2 | — | — | — | — |
| Menthone | — | — | — | — | 0.2 | — | — | — |
| Cineol | — | — | — | — | — | 0.2 | — | — |
| Borneol | — | — | — | — | — | — | 0.2 | — |
| Beta-pinene | — | — | — | — | — | — | — | 0.2 |

TABLE 13-continued

| Formulation | Inventive Composition | | | | | | | |
|---|---|---|---|---|---|---|---|---|
| | 49 | 50 | 51 | 52 | 53 | 54 | 55 | 56 |
| Methylated beta-cyclodextrin (Ether substitution degree = 1.2) | 1 | 1 | 1 | 1 | 1 | 1 | 1 | 1 |
| Ion exchanged water | balance | → | → | → | → | → | → | → |

What is claimed is:

1. A liquid shampoo composition comprising the following three components (A), (B) and (C):
   (A) 5 to 30 wt % of at least one surface active agent,
   (B) 0.05 to 5 wt % of a skin sensation inducing aromatic chemical selected from the group consisting of menthol, camphor, methyl salicylate, cineol, menthone, piperitone, borneol, beta-pinene, menthyl acetate and varylamide nonylate,
   (C) ½ to twenty times by weight based on the amount of component (B) of a modified cyclodextrin represented by the following formula (I) or (II):

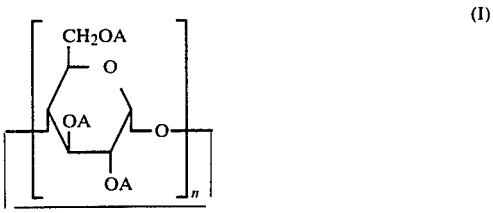

(I)

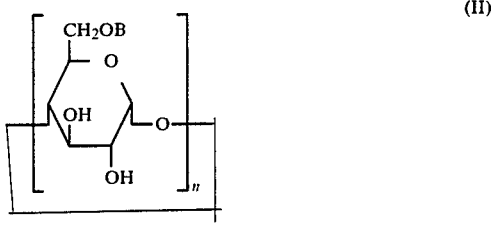

(II)

in which n represents a number from 6 to 9, A represents a hydrogen atom or a methyl group, and B represents a hydrogen atom or the group (III)

(III)

with the proviso that neither an ether substitution number of methyl group nor a substitution number of group (III) is less than 1.

2. The liquid shampoo composition according to claim 1, in which said modified cyclodextrin (C) is a methylated beta-cyclodextrin of n=7 in formula (I) having an ether substitution degree ranging from 1.14 to 1.60.

3. The liquid shampoo composition according to claim 2, in which 50 wt % or more of said methylated beta-cyclodextrin has an ether substitution number ranging from 8 to 11.

4. A liquid shampoo composition comprising the following four components (A) to (D):
   (A) 5 to 30 wt % of at least one surface active agent,
   (B) 0.05 to 5 wt % a skin sensation inducing aromatic chemical selected from the group consisting of menthol, camphor, methyl salicylate, cineol, menthone, piperitone, borneol, beta-pinene, menthyl acetate and varylamide nonylate, (C) ½ to twenty times by weight based on the amount of component (B) of a modified cyclodextrin represented by the following formula (I) or (II):

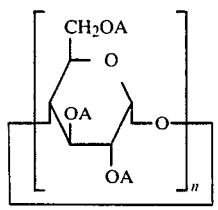

(I)

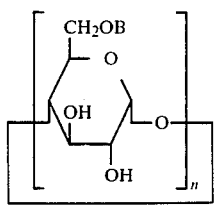

(II)

in which n represents a number from 6 to 9, A represents a hydrogen atom or a methyl group, and B represents a hydrogen atom or the group (III)

$$-CH_2CHCH_2N^{\oplus}(CH_3)_3 \cdot Cl^{\ominus} \qquad (III)$$
$$\phantom{-CH_2C}|$$
$$\phantom{-CH_2CH}OH$$

with the proviso that neither an ether substitution number of methyl group nor a substitution number of group (III) is less than 1, (D) 3 to 20 wt % of urea.

5. The liquid shampoo composition according to claim 4, in which said modified cyclodextrin (C) is a methylated beta-cyclodextrin of $n=7$ in formula (I) having an ether substitution degree ranging from 1.14 to 1.60.

6. The liquid shampoo composition according to claim 5, in which 50 wt % or more of said methylated beta-cyclodextrin has an ether substitution number ranging from 8 to 11.

* * * * *